United States Patent
Burton et al.

(10) Patent No.: US 8,951,973 B2
(45) Date of Patent: Feb. 10, 2015

(54) CONTROLLED-RELEASED PEPTIDE FORMULATIONS

(76) Inventors: Kevin Burton, Hoover, AL (US); Torsten Woehr, Marblehead, MA (US); Thomas R. Tice, Indian Springs, AL (US); Mimoun Ayoub, Otelfingen (CH)

( * ) Notice: Subject to any disclaimer, the term of this patent is extended or adjusted under 35 U.S.C. 154(b) by 953 days.

(21) Appl. No.: 13/060,676

(22) PCT Filed: Aug. 28, 2009

(86) PCT No.: PCT/US2009/055461
§ 371 (c)(1),
(2), (4) Date: May 16, 2011

(87) PCT Pub. No.: WO2010/025435
PCT Pub. Date: Mar. 4, 2010

(65) Prior Publication Data
US 2012/0027805 A1    Feb. 2, 2012

Related U.S. Application Data (60) Provisional application No. 61/093,258, filed on Aug. 29, 2008.

(51) Int. Cl.
| | |
|---|---|
| A61K 38/10 | (2006.01) |
| C07K 7/00 | (2006.01) |
| C07K 7/06 | (2006.01) |
| A61K 38/08 | (2006.01) |
| C08K 9/10 | (2006.01) |
| A61K 9/16 | (2006.01) |
| A61K 38/00 | (2006.01) |

(52) U.S. Cl.
CPC .............. *A61K 9/1647* (2013.01); *A61K 38/00* (2013.01)
USPC ........................ 514/21.4; 514/21.6; 523/207

(58) Field of Classification Search
None
See application file for complete search history.

(56) References Cited

U.S. PATENT DOCUMENTS

| | | | | |
|---|---|---|---|---|
| 5,538,739 | A | * | 7/1996 | Bodmer et al. ............... 424/501 |
| 5,776,885 | A | | 7/1998 | Orsolini et al. |
| 5,776,886 | A | | 7/1998 | Inamoto et al. |
| 6,706,289 | B2 | | 3/2004 | Lewis et al. |
| 7,326,425 | B2 | | 2/2008 | Kohn et al. |
| 2007/0092574 | A1 | | 4/2007 | Cook |
| 2007/0116772 | A1 | | 5/2007 | Sung et al. |

FOREIGN PATENT DOCUMENTS

| | | | |
|---|---|---|---|
| EP | 0721776 | A1 | 5/2002 |
| EP | 1666031 | A1 | 6/2006 |
| WO | WO 98/24427 | | 6/1998 |
| WO | WO 00/40259 | | 7/2000 |
| WO | WO-2007/084527 | * | 7/2007 |

OTHER PUBLICATIONS

Chasin, M., "Biodegradable polymers for controlled drug delivery." In: Hollinger, Jo, editor, Biomedical Applications of Synthetic Biodegradable Polymers CRC, p. 1-15 (1995).
Hayashi, T., "Biodegradable polymers for biomedical uses," Prog. Polym. Sci. vol. 19:663-700 (1994).
Tamber, H, et al., "Formulation aspects of biodegradable polymeric microspheres for antigen delivery," Advanced Drug Delivery Reviews, 57:357-376 (2005).
Simon, et al., "Peptidis: A modular approach to drug discovery," PNAS USA, vol. 89:9367-9371 (1992).

* cited by examiner

*Primary Examiner* — Satyanarayana R Gudibande
(74) *Attorney, Agent, or Firm* — Todd Lorenz, Esq.; Arnold & Porter LLP (57) ABSTRACT

Described herein are methods and compositions for modulating the release and/or drug loading characteristics of encapsulated bioactive agents in polymer-based delivery systems via direct modification of the isoelectric point and/or net charge of the bioactive agent.

8 Claims, 9 Drawing Sheets

FIG. 1

Figure 2: Drug Loading

Figure 3: Loading Efficiency

Figure 4: Particle Size

Figure 5: In vitro release rate, PLG 50:50 2A

Figure 6: In vitro release rate, PLG 50:50 2A, through 14 days

Figure 7: In vitro release rate, PLG 50:50 2E

Figure 8: In vitro release rate, PLG 85:15 2E

Figure 9: In vitro release rate, PLG 85:15 2.5E

Figure 10: In vitro release rate, PLG 85:15 2E through 15 days

# CONTROLLED-RELEASED PEPTIDE FORMULATIONS

FIELD

The invention relates to peptide formulations, and more specifically to methods and compositions for modifying the release and/or drug-loading characteristics of such formulations.

BACKGROUND OF THE INVENTION

The importance of biocompatible and/or biodegradable polymers as carriers for active therapeutic agents is well established. Biocompatible, biodegradable, and relatively inert polymers such as poly(lactide) (PL) or poly(lactide-co-glycolide) (PLGA) containing a bioactive agent are commonly utilized in controlled-release delivery systems (for review, see M. Chasin, Biodegradable polymers for controlled drug delivery. In: J. O. Hollinger Editor, Biomedical Applications of Synthetic Biodegradable Polymers CRC, Boca Raton, Fla. (1995), pp. 1-15; T. Hayashi, Biodegradable polymers for biomedical uses. Prog. Polym. Sci. 19 4 (1994), pp. 663-700; and Harjit Tamber, Pal Johansen, Hans P. Merkle and Bruno Gander, Formulation aspects of biodegradable polymeric microspheres for antigen delivery, Advanced Drug Delivery Reviews, Volume 57, Issue 3, 10 Jan. 2005, Pages 357-376).

With respect to the delivery of therapeutic peptides in particular, however, there still exist many challenges to the design of effective controlled-release, polymer-based delivery systems. A basic requirement for such delivery systems is appropriate control over the release of the encapsulated active agent, an objective which is complicated by variations in the release kinetics of polymer systems. Generally, an initial diffusional or burst release phase from the intact polymer system is followed by a slower lag phase leading to an erosional release phase as the polymer system begins to degrade. It is important to maintain the concentration of the peptide molecule within a therapeutically effective window throughout both of the principal peptide release phases and to avoid excessive concentrations, and particularly an initial burst during the diffusional release phase, which may lead to adverse side effects or untoward results. In this respect, however, wide variation in the size, charge and conformation of different peptide molecules has thus far prevented a more uniform approach to their effective encapsulation.

The prior art describes various strategies for improving controlled-release delivery from polymer-based delivery systems including the use of new polymeric materials and polymer blends, and/or the incorporation of additives in such systems to help facilitate drug release. U.S. Pat. No. 7,326, 425, for example, describes a blended polymer-based delivery system having a first polymer capable of forming hydrogen bonds with a desired bioactive agent to prevent bursts, and a second polymer the degradation products of which trigger the release of the active agent from the first polymer. Alternatively, U.S. Patent Publication No. 2007/0092574 describes the addition of certain organic ions to polymer-based delivery systems encapsulating water-soluble bioactive agents to reduce the burst release and degradation of the bioactive agent, wherein the organic ion is selected to neutralize the overall charge of a particular bioactive agent.

In each of these examples, however, and in the prior art in general, the primary focus of such strategies is on manipulation of the polymer-based delivery system to suit the requirements of a particular bioactive agent, as opposed to manipulation or adaptation of the bioactive agent itself.

SUMMARY OF THE INVENTION

In contravention of the conventional formulation methodology of manipulating the polymer-based delivery system to suit the encapsulated agent, the present invention provides methods and compositions for modulating the release and/or drug-loading characteristics of an encapsulated bioactive agent through direct modification of the bioactive agents themselves. As demonstrated herein, modification of the isoelectric point of a bioactive agent such as a peptide molecule, e.g., alteration of the overall charge of the peptide, can predictably modify the release and/or loading characteristics of polymer-based delivery systems in clinically meaningful ways including, e.g., reducing or enhancing the initial diffusional release of the peptide from the polymer-based delivery system, modulating the erosional release rate from biodegradable systems, and/or increasing the encapsulation efficiency of such peptides.

In one aspect, methods for increasing bioactive agent loading efficiency in polymer-based delivery systems are provided, comprising modifying the isoelectric point of the agent prior to encapsulation in a polymer-based delivery system. In one embodiment, the isoelectric point of the agent is modified such that it carries a more positive charge compared to the parent molecule in the environment of the desired polymer-based delivery system.

In one embodiment, methods for increasing bioactive agent loading efficiency in polymer-based delivery systems are provided, comprising adding additional positive charge to a parent molecule.

In one aspect, methods for modulating the erosional release rate of a bioactive agent from a biodegradable polymer-based delivery system are provided, comprising changing the isoelectric point of the agent prior to encapsulation in the polymer-based delivery system. In one embodiment, the isoelectric point of an agent is quantitatively increased or decreased such that it carries a greater net positive or negative charge, respectively, compared to the parent molecule in the environment of the desired polymer-based delivery system.

In one embodiment, methods for increasing the erosional release rate of a bioactive agent from a biodegradable polymer-based delivery system are provided, comprising adding additional positive or negative charge to a parent molecule to produce a stoichiometric increase or decrease, respectively, in net charge relative to the parent molecule. In one embodiment, additional positive charge is added to a neutral or cationic parent molecule to increase the erosional release rate. In another embodiment, additional negative charge is added to a neutral or anionic parent molecule to increase the erosional release rate. In a preferred embodiment, acid-terminated polymer-based delivery systems are employed for enhanced effect.

Surprisingly, the present inventors have determined that an increase in the net positive charge of a bioactive agent relative to a cationic parent molecule can work as well as, and in some cases even better than, a reduction in or neutralization of the net charge to increase the erosional release rate of such an agent from a biodegradable polymer-based delivery system. Significantly, as also demonstrated for the first time herein, creating a greater charge density in a charged bioactive agent relative to a parent molecule provides for greater effect.

In one aspect, methods for modulating the initial diffusional release of a bioactive agent from a polymer-based delivery system are also provided, comprising changing the isoelectric point of the agent prior to encapsulation in the polymer-based delivery system. In one embodiment, the isoelectric point of the agent is increased or decreased such that it carries a greater net positive or negative charge, respectively, relative to the parent molecule in the environment of the desired polymer-based delivery system.

In one embodiment, methods for increasing the initial diffusional release of a bioactive agent from a polymer-based delivery system are provided, comprising adding additional positive charge to the parent molecule to produce a stoichiometric increase in net charge relative to the parent molecule. In a preferred embodiment, ester-terminated polymer-based delivery systems are employed for enhanced effect.

In one embodiment, methods for decreasing the initial diffusional release of a bioactive agent from a polymer-based delivery system are provided, comprising adding additional negative charge to the parent molecule to produce a stoichiometric decrease in net charge relative to the parent molecule. In a preferred embodiment, ester-terminated polymer-based delivery systems are employed for enhanced effect.

Any suitable means for modifying the isoelectric point of a bioactive agent can be employed in conjunction with the subject methods including, e.g., chemical modification, amino acid substitution, conjugation of positively or negatively-charged accessory molecules, and more preferably cleavable accessory molecules, and the like. The additional positive or negative charge may be distributed uniformly or non-uniformly across the bioactive agent, and is preferably implemented at a location distal to the known site(s) of action of the parent molecule, e.g. binding site, etc. In one embodiment, the additional charge distribution is clustered at the amino or carboxy terminus. In another embodiment, the additional charge is conjugated to an amino acid side chain.

Modification of the isoelectric point as disclosed herein may also be employed in conjunction with more conventional techniques such as conversion to water insoluble addition salts (e.g., U.S. Pat. No. 5,776,886), pegylation (U.S. Pat. No. 6,706,289), and the like, to further modulate release kinetics and/or loading efficiency. In a further aspect, improved controlled-release pharmaceutical compositions are provided comprising bioactive agents modified according to the above methods and encapsulated in polymer-based delivery systems.

In one embodiment, the controlled-release pharmaceutical composition comprises a modified bioactive agent encapsulated by a polymer, wherein the isoelectric point of the modified bioactive agent has been increased relative to the parent molecule to increase drug loading efficiency, and/or to increase the erosional release rate of the modified bioactive agent, preferably from an acid-terminated polymer system, and/or to increase the diffusional release of the modified bioactive agent, preferably from an ester-terminated polymer system. In one such embodiment, the parent molecule is neutral or cationic.

In another embodiment, the controlled-release pharmaceutical composition comprises a modified bioactive agent encapsulated by a biodegradable polymer, wherein the isoelectric point of the modified bioactive agent has been decreased relative to the parent molecule to increase the erosional release rate of the modified bioactive agent, preferably from an acid-terminated polymer system, and/or to decrease the diffusional release rate of the modified bioactive agent, preferably from an ester-terminated polymer system, relative to the parent molecule. In one such embodiment, the parent molecule is neutral or anionic.

Unless otherwise specified, the compositions described herein may comprise a non-biodegradable polymer-based delivery system, e.g., a polymer system comprising a non-biodegradable polymer. In one aspect, the non-biodegradable polymer is selected from the group consisting of polyacrylates, polymers of ethylene-vinyl acetates and other acyl substituted cellulose acetates, non-degradable polyurethanes, polystyrenes, polyvinyl chloride, polyvinyl fluoride, poly(vinyl imidazole), chlorosulphonate polyolefins, polyethylene oxide, blends and copolymers thereof.

In another aspect, the compositions described herein may comprise a biodegradable polymer-based delivery system, e.g., a polymer system comprising a biodegradable polymer. In another aspect, the biodegradable polymer is selected from the group consisting of homopolymers of poly(lactic acid) (PLA), polylactide (PL) or poly(glycolic acid) (PGA), polyglycolide (PG), poly(lactic acid)-co-(glycolic acid) (PLGA), poly(actide-co-glycolide (PLG), poly(ortho esters), and polyanhydrides. Due to the biocompatibility and the long history of their clinical applications, PLGA and PLA are most generally used. Other biodegradable polymers that may be used include polycaprolactone, polycarbonates, polyesteramides, poly(amino acids), poly(dioxanones), poly(alkylene alkylate)s, polyacetals, polycyanoacrylates, biodegradable polyurethanes, blends and copolymers thereof.

The subject compositions and methods find advantageous use with a variety of bioactive agents, including therapeutic proteins, nucleic acids, peptides, polypeptides, oligonucleotides, and the like.

In another aspect, the invention provides methods of treating a patient in need of treatment, comprising administering a therapeutically effective amount of a pharmaceutical composition of the invention to the patient.

BRIEF DESCRIPTION OF THE DRAWINGS

FIG. 1 is an exemplary schematic of a hypothesized triphasic drug release from a degradable matrix.

FIG. 2 shows the actual loading (y-axis) of five peptides (DP1, DP2, DP3, DP4, and DP5) with a neutral, positive (+) or negative (−) charge overall (x-axis). Unless otherwise noted, each peptide molecule was loaded into the polymer as an acetate salt.

FIG. 3 shows the percent theoretical loading efficiency (y-axis) of five peptides (DP1, DP2, DP3, DP4, and DP5) with a neutral, positive (+) or negative (−) charge overall (x-axis). Unless otherwise noted, each peptide molecule was loaded into the polymer as an acetate salt.

FIG. 4 shows the mean particle size (μM) of five peptides (DP1, DP2, DP3, DP4, and DP5) with a neutral, positive (+) or negative (−) charge overall (x-axis). Unless otherwise noted, each peptide molecule was loaded into the polymer as an acetate salt.

FIG. 5 shows the release rate as percent release (y-axis) of five peptides (DP1, DP2, DP3, DP4, and DP5) with a neutral, positive (+) or negative (−) charge overall over 35 days (x-axis) from a microparticle, polymer-based formulation containing an acid-terminated, 50:50 poly(lactide-co-glycolide) with an approximate i.v. of 0.2 dL/g as measured in chloroform at a concentration of 0.5 g/dL at 30° C. Unless otherwise noted, each peptide molecule was loaded into the polymer as an acetate salt.

FIG. 6 shows the release rate as percent release (y-axis) of five peptides (DP1, DP2, DP3, DP4, and DP5) with a neutral, positive (+) or negative (−) charge overall over 14 days (x-axis) from a microparticle, polymer-based formulation containing an acid-terminated, 50:50 poly(lactide-co-glycolide) with an approximate intrinsic viscosity (i.v.) of 0.2 dL/g as measured in chloroform at a concentration of 0.5 g/dL at 30° C. Unless otherwise noted, each peptide molecule was loaded into the polymer as an acetate salt.

DETAILED DESCRIPTION

Methods and formulations are provided for the controlled-release of bioactive agents from polymer-based delivery systems through direct modification of the bioactive agent. As described herein, the isoelectric point of the modified bioactive agent may be changed relative to a parent molecule, and/or the net charge of the modified bioactive agent may be changed relative to a parent molecule, etc. Encapsulated formulations comprising such modified bioactive agents have enhanced controlled-release properties, e.g., a lower initial diffusional or burst release, an increased erosional release rate, increased encapsulation efficiency, etc., compared to formulations comprising similarly encapsulated formulations of the parent molecule.

Release of a bioactive agent from a polymer, e.g., a biodegradable polymer such as a PLG microparticle, generally follows a triphasic release profile as exemplified in FIG. 1. Phase 1 may generally be characterized as a diffusional release or "burst" effect, during which the initial release rate of the modified peptide molecule may be rapid, and may be dependent on hydration of the polymer (occurring within minutes), swelling of the matrix (hours), dissolution of the modified peptide molecule (minutes) and diffusion from the matrix (hours).

The second phase of release (Phase 2, FIG. 1) may be referred to as the induction or lag phase, and may be characterized by a period of slower or no release. Phase 2 may be associated with the time required for pores or channels to form or time for water to fill such pores or channels in the polymer matrix thereby allowing access to the modified peptide molecule entrapped within the polymer matrix.

When a biodegradable polymer-based delivery system is used, and as biodegradable polymer degradation continues, diffusional paths may be formed through the eroding matrix, which may allow the modified peptide molecule to travel down a concentration gradient and escape the matrix. This erosional release corresponds to the third phase of release as demonstrated in FIG. 1.

Release of a bioactive agent from a non-biodegradable polymer generally follows a biphasic release profile, in which phase 1 corresponds to a diffusional release of the bioactive peptide and phase 2 corresponds to a lag phase. Accordingly, skilled artisans are generally familiar with typical release rates of bioactive agents from such polymer-based delivery systems.

In one embodiment, improved controlled-release compositions and methods are provided wherein the isoelectric point of a parent molecule is increased to produce a modified bioactive agent having a more positive net charge and/or charge density, which as demonstrated herein can increase drug-loading efficiency, increase the erosional release rate of the modified bioactive agent, and particularly from acid-terminated polymer-based systems, and/or increase the diffusional release of the modified bioactive agent, and particularly from ester-terminated polymer-based systems, relative to the parent molecule. In one such embodiment, the parent molecule is neutral or cationic.

In another embodiment, improved controlled-release compositions and methods are provided wherein the isoelectric point of a parent molecule is decreased to produce a modified bioactive agent having a more negative net charge and/or charge density, which as demonstrated herein can increase the erosional release rate of the modified bioactive agent, and particularly from acid-terminated polymer-based systems, and/or decrease the diffusional release rate of the modified bioactive agent, and particularly from ester-terminated polymer-based systems, relative to the parent molecule. In one such embodiment, the parent molecule is neutral or anionic.

"Bioactive agent" as used herein refers to any therapeutic protein, therapeutic antibody, nucleic acid, peptide, polypeptide, oligonucleotide, aptamer or other biologically active compound for administration to a subject.

By "peptide molecule" as used herein is meant a polymeric molecule comprising at least two amino acids covalently linked by a peptide bond, and includes a protein, a polypeptide, an oligopeptide and a peptide. A peptide molecule may be made up of naturally occurring amino acids and peptide bonds, or synthetic peptidomimetic structures, i.e., "analogs", such as peptoids (see Simon et al., 1992, Proc Natl Acad Sci USA 89(20):9367, incorporated by reference).

By "amino acid" and "amino acid identity" as used herein is meant one of the twenty naturally occurring amino acids or any non-natural analogues that may be present at a specific, defined position. Thus "amino acid", or "peptide residue", as used herein means both naturally occurring and synthetic amino acids (including analogues of naturally occurring amino acids). For example, homophenylalanine, citrulline, 2-amino-3-guanidinoproprionic acid, 2-amino-3-ureidoproprionic acid, Lys(Me), $Lys(Me)_2$, $Lys(Me)_3$, Ornitine, Omega-nitro-arginine, Arg(Me)2, α-methyl Arg, α-methyl Lys, β homolysine, β homoarginine, noreleucine, and the like are considered amino acids for the purposes of the invention. "Amino acid" also includes imino acid residues such as proline and hydroxyproline. The side chain may be in either the (R) or the (S) configuration, and may be either D- or L-isomers. In the preferred embodiment, the amino acids are in the (S) or L-configuration, although D-isomers may be used to improve serum stability. If non-naturally occurring side chains are used, non-amino acid substituents may be used, for example to prevent or retard in vivo degradation.

"Parent molecule" as used herein refers to a bioactive agent that is subsequently modified in accordance with the invention teachings to generate a "modified bioactive agent." In some embodiments, a parent molecule may be any bioactive agent molecule requiring a controlled-release, polymer-based formulation for therapeutic use. As described herein, encapsulation and release from polymers can be manipulated by modification of the parent molecule, e.g., modification of the isoelectric point, net charge, solubility etc. of the parent molecule.

Similarly, by "parent peptide molecule," "parent polypeptide," "parent protein," and the like as used herein is meant a polypeptide, protein and the like that is subsequently modified to generate a "modified peptide molecule." For example, a parent peptide molecule, a parent polypeptide, a parent protein or the like may serve as a template and/or basis for at least one modification described herein, e.g., modification of the isoelectric point, modification of the net charge, modification of the solubility, etc. Said parent peptide molecule may be a naturally occurring polypeptide, or a variant or engineered version of a naturally occurring polypeptide. Parent polypeptide may refer to the polypeptide itself, compositions that comprise the parent polypeptide, or the amino acid sequence that encodes it.

By "isolectric point", "pI", or the like as used herein is meant the pH at which a peptide molecule carries no net electrical charge. The isoelectric point may be determined using well known methods, e.g., by isoelectric focusing. In case of smaller peptide molecules the approximate pI may be also calculated. In general, the pI of a peptide molecule depends on the pKa values of its basic and acidic groups, e.g., in case of a peptide formed with encoded amino acids only, the primary amine of the N-terminus or the lysine side chain, the guanidine group of the arginine side chain, the imidazole ring system of histidine and the carboxylic acid groups of the peptide C-terminus, the aspartic acid side chain and glutamic acid side chain.

Modification of the pI of a parent peptide molecule may occur by, e.g., chemical modification. Non-limiting examples of such modifications include acylation, alkylation or other chemical modification of the N-terminal amine group; amidation, esterification or other chemical modification of the C-terminal carboxylic acid group; substitution of a non-ionizable amino acid residue for a lysine, histidine, arginine, glutamic acid, aspartic acid or other non-encoded amino acids with acidic or basic chain groups; acylation, alkylation or other chemical modification of side chain groups of lysine, histidine, arginine or basic functions of other, non-encoded amino acids; amidation, esterification or other chemical modification of side chain carboxylic acid groups, conjugation with pI shifting accessory molecules. etc. In case of ionized peptides the pI of the salt form also depends on the $pK_a$ of the counter ion.

As used herein, the "net charge" of a parent peptide molecule depends on its pI and the pH of the peptide solution. The net charge of a parent peptide molecule may be modified by any of the following non-limiting examples: acylation, alkylation or other chemical modification of the N-terminal amine group; amidation, esterification or other chemical modification of the C-terminal carboxylic acid group; substitution of a non-ionizable amino acid residue for a lysine, histidine, arginine, glutamic acid, aspartic acid or other non-encoded amino acid with acidic or basic chain groups; modification of the isoelectric point of the parent peptide; conjugation with positively or negatively charged accessory molecules, and the like.

As disclosed herein, modification of charge distribution and/or density can also be considered for modulation of polymer encapsulation and release properties of the parent peptide. Added charge density may be distributed uniformly or non-uniformly across the modified peptide molecule. In one embodiment, a non-uniform distribution of additional negative or positive charge comprises clustering the additional negative or positive charge, respectively, at one or more positions within the peptide chain. The cluster(s) of additional negative or positive charge may be anywhere along the peptide, e.g., near or at the end of the peptide, near or at the center of the peptide, etc., but are preferably positioned distal to the active site of the peptide, which can be readily determined by reference to the known characteristics of the parent molecule. Alternatively, the additional negative or positive charge may be distributed evenly along the polymer.

In one embodiment, a modified peptide molecule may comprise an additional negative or positive charge relative to its parent peptide molecule, e.g., via substitution of appropriate amino acids. In one embodiment, the addition of positive charge is accomplished by substitution of negative and/or non-ionizable amino acids in the parent peptide molecule with lysine, arginine, histidine, or analogues thereof. In another embodiment, the addition of negative charge is accomplished by substitution of positive and/or non-ionizable amino acids in the parent peptide molecule with glycine, aspartic acid, glutamic acid, or analogues thereof (e.g., any alpha or beta amino alkanedioic acid (e.g., amino suberic acid).

In one embodiment, a modified peptide molecule may comprise an additional negative or positive charge relative to its parent peptide molecule, e.g., via conjugation with one or more negatively-charged accessory molecule(s) or positively-charged accessory molecule(s), respectively. "Conjugation" as used herein refers to covalent linkage of two molecules as opposed to mere complexation or other close physical association. Exemplary negatively-charged accessory molecules include conjugations of in general any chemical functionality of a peptide such as the hydroxyl group of tyrosine, threonine and serine side chains, the thiol group of the cysteine side chain or the N-terminal amino group or amino groups of the arginine and lysine side chains with phospholipids (phosphoamid bound), mono-, di-, and/or tri-phosphates, sulphates, citrates, tartaric acids, polyaspartic, polyglutamic and diacids (e.g. oxalic acids, malonic acids, succinic acids, etc.). Exemplary negatively-charged structures also include, but are not limited to, poly(glutamic acid), anionic lipids, poly(aspartic acid), and alginates. In some cases the chemical functionality of the peptide may also have to be induced or introduced in order to facilitate conjugation (e.g. formation of reactive thioesters, aldhydes, hydroxylamines, alkylbromides, maleimides, etc). Exemplary positively-charged accessory molecules include, polylysine, polyarginine, polyhistidine, poly(allyl amine), poly(ethyl imine), chitosan or positively charged lipid structures.

Accessory molecules may also comprise a "tail" of positive or negative amino acids, and may be conjugated to the bioactive agent by a more neutral linker moiety, e.g., polyethylene glycol (PEG), poly —$CH_2$—, and the like.

Modified peptide molecules may further include pharmaceutically acceptable counterions, representative examples of which are set forth in Table 1 below.

TABLE 1

Potential counterions

| Salt Class | Examples |
|---|---|
| inorganic acids | hydrochloride, sulfate, nitrate, phosphate |
| sulfonic acids | tosylate, mesylate, esylate, isethionate |
| carboxylic acids | acetate, proprionate, maleate, benzoate, salicylate, fumarate |
| hydroxyacids | citrate, lactate, succinate, tartrate, glycollate |
| anionic amino acids | glutamate, aspartate |
| fatty acids | stearate, hexanoate, octanoate, decanoate, oleate |

Modification of solubility in water and/or organic solvents as well as alteration of the hydrophilicity of a parent peptide molecule may also be employed in conjunction with the subject methods to further modulate the encapsulation and release characteristics of a peptide in a polymer-based delivery system. The solubility and/or hydrophilicity of a peptide therapeutic may be modified by changing its salt form or by pegylation as described in, e.g., U.S. Pat. No. 5,776,885 and No. 6,706,289, the disclosures of which are both expressly incorporated by reference herein.

As used herein "relative to a parent peptide molecule" refers to a change (e.g., an increase or decrease) in a quantifiable characteristic, e.g., isoelectric point, net charge, etc., by a modified peptide compared to the parent peptide molecule (e.g., the peptide molecule that was subsequently modified to generate the modified peptide molecule) when the amounts of modified peptide molecule and parent peptide molecule are essentially the same in the same assay.

Described herein are methods and compositions for modulating the release and/or drug loading characteristics of encapsulated peptide molecules in polymer-based delivery systems through direct modification of the peptide molecules themselves. Polymer-based delivery systems described herein are generally biocompatible polymer-based delivery system. The polymer-based delivery systems described herein may comprise a biodegradable or non-biodegradable polymer, blends or copolymers thereof. A polymer-based delivery system, or a polymer, is biocompatible if the polymer, and any degradation products of the polymer, are non-toxic to the recipient and also present no significant deleterious or untoward effects on the recipient's body.

Biocompatible, non-biodegradable polymers suitable for encapsulating bioactive agents (e.g., peptide molecules) include, but are not limited to, non-biodegradable polymers selected from the group consisting of polyacrylates, polymers of ethylene-vinyl acetates and other acyl substituted cellulose acetates, non-degradable polyurethanes, polystyrenes, polyvinyl chloride, polyvinyl fluoride, poly(vinyl imidazole), chlorosulphonate polyolefins, polyethylene oxide, blends and copolymers thereof.

Biodegradable polymers may also be used for encapsulating bioactive agents (e.g., peptide molecules) e.g., for controlled-release formulations. In one embodiment, biodegradable polymers for which the degradation products are known to be innocuous or biocompatible are used. Accordingly, such biodegradable polymers need not be surgically removed at the end of a treatment. Commonly used biodegradable polymers, which have been investigated for the controlled-release of peptide molecules, include homopolymers of poly(lactic acid) (PLA), polylactide (PL) or poly(glycolic acid) (PGA), polyglycol(de (PG), poly(lactic acid)-co-(glycolic acid) (PLGA), poly(actide-co-glycolide (PLG), poly(ortho esters), and polyanhydrides. Due to the biocompatibility and the long history of clinical applications. PLG and PL are most generally used. Other biodegradable polymers that may be used include polycaprolactone, polycarbonates, polyesteramides, poly(amino acids), poly(dioxanones), poly(alkylene alkylate)s, polyacetals, polycyanoacrylates, biodegradable polyurethanes, blends and copolymers thereof.

In one aspect, polymeric delivery systems can be microparticles including, but not limited to microspheres, microcapsules, nanospheres and nanoparticles comprising biodegradable polymeric excipients, non-biodegradable polymeric excipients, or mixtures of polymeric excipients thereof, or the polymeric delivery systems can be, but not limited to rods or other various shaped implants, wafers, fibers, films, in situ forming boluses and the like comprising biodegradable polymeric excipients, non-biodegradable polymeric excipients, or mixtures thereof. These systems can be made from a single polymeric excipient or a mixture or blend of two or more polymeric excipients.

The term "microparticle" is used herein to include nanoparticles, microspheres, nanospheres, microcapsules, nanocapsules, and particles, in general. As such, the term microparticle refers to particles having a variety of internal structure and organizations including homogeneous matrices such as microspheres (and nanospheres) or heterogeneous core-shell matrices (such as microcapsules (and nanocapsules), porous particles, multi-layer particles, among others. Microparticles are particles that have sizes in the range of about 10 nanometers to about 1000 micrometers (microns).

A variety of techniques known in the art can be used to form microparticles including e.g., single or double emulsion steps followed by solvent removal. Solvent removal may be accomplished by extraction, evaporation or spray drying among other methods.

In the solvent extraction method, the polymer is dissolved in an organic solvent that is at least partially soluble in the extraction solvent such as water. The modified bioactive agent, either in soluble form or dispersed as fine particles, is then added to the polymer solution, and the mixture is dispersed into an aqueous phase that contains a surface-active agent such as poly(vinyl alcohol). The resulting emulsion is added to a larger volume of water where the organic solvent is removed from the polymer/bioactive agent to form hardened microparticles.

In the solvent-evaporation method, the polymer is dissolved in a volatile organic solvent. The bioactive agent, either in soluble form or dispersed as fine particles, is then added to the polymer solution, and the mixture is suspended in an aqueous phase that contains a surface-active agent such as poly(vinyl alcohol). The resulting emulsion is stirred until most of the organic solvent evaporates, leaving internally, solid microparticles.

In the spray drying method, the polymer is dissolved in a suitable solvent, such as methylene chloride (e.g., 0.04 g/mL). A known amount of the modified bioactive agent is then suspended (if insoluble) or co-dissolved (if soluble) in the polymer solution. The solution or the dispersion is then spray dried. Microparticles ranging in diameter between one and ten microns can be obtained with a morphology, which depends on the selection of polymer.

Other known methods, such as phase separation and coacervation, and variations of the above, are known in the art and also may be employed in the present invention.

A suitable polymeric excipient includes, but is not limited to, a poly(diene) such as poly(butadiene) and the like; a poly(alkene) such as polyethylene, polypropylene, and the like; a poly(acrylic) such as poly(acrylic acid) and the like; a poly(methacrylic) such as poly(methyl methacrylate), a poly(hydroxyethyl methacrylate), and the like; a poly(vinyl ether); a poly(vinyl alcohol); a poly(vinyl ketone); a poly(vinyl halide) such as poly(vinyl chloride) and the like; a poly(vinyl nitrile), a poly(vinyl ester) such as poly(vinyl acetate) and the like; a poly(vinyl pyridine) such as poly(2-vinyl pyridine), poly(5-methyl-2-vinyl pyridine) and the like; a poly(styrene); a poly (carbonate); a poly(ester); a poly(orthoester) including a copolymer; a poly(esteramide); a poly(anhydride); a poly (urethane); a poly(amide); a cellulose ether such as methyl cellulose, hydroxyethyl cellulose, hydroxypropyl methyl cellulose, and the like; a cellulose ester such as cellulose acetate, cellulose acetate phthalate, cellulose acetate butyrate, and the like; a poly(saccharide), a protein, gelatin, starch, gum, a resin, and the like. These materials may be used alone, as physical mixtures (blends), or as co-polymers. Derivatives of any of the polymers listed above are also contemplated.

In one aspect, the polymeric excipient of the delivery system includes a biocompatible, non-biodegradable polymer such as, for example, a silicone, a polyacrylate; a polymer of ethylene-vinyl acetate; an acyl substituted cellulose acetate; a non-degradable polyurethane; a polystyrene; a polyvinyl chloride; a polyvinyl fluoride; a poly(vinyl imidazole); a chlorosulphonate polyolefin; a polyethylene oxide; or a blend or copolymer thereof.

In another aspect, the polymeric excipient includes a biocompatible, biodegradable polymer such as, for example, a poly(lactide); a poly(glycolide); a poly(lactide-co-glycolide); a polylactic acid); a poly(glycolic acid); a poly(lactic acid-co-glycolic acid); a poly(caprolactone); a poly(orthoester); a poly(phosphazene); a poly(hydroxybutyrate) or a copolymer containing a poly(hydroxybutarate); a poly(lactide-co-caprolactone); a polycarbonate; a polyesteramide; a polyanhydride; a poly(dioxanone); a poly(alkylene alkylate); a copolymer of polyethylene glycol and a polyorthoester; a biodegradable polyurethane; a poly(amino acid); a polyetherester; a polyacetal; a polycyanoacrylate; a poly(oxyethylene)/poly(oxypropylene)copolymer, or a blend or copolymer thereof.

In one aspect, the polymer-based delivery system comprises a non-biodegradable polymer. In another aspect, the polymer-based delivery system comprises a biodegradable polymer, wherein the peptide is imbedded within the polymer of the delivery system. In one aspect, the peptide is encapsulated in a delivery system composed of poly(lactide-co-glycolide), poly(lactide), poly(glycolide), polycaprolactone, poly(lactide-co-caprolactone), poly(lactide-co-glycolide-co-caprolactone), poly(glycolide-co-caprolactone), or a mixture thereof. Lactide/glycolide polymers for drug-delivery formulations are typically made by melt polymerization through the ring opening of lactide and glycolide monomers. Some polymers are available with or without carboxylic acid end groups. Some polymers are available with a block of polyethylene glycol (PEG). When the end group of the poly(lactide-co-glycolide), poly(lactide), or poly(glycolide) is not a carboxylic acid, for example, an ester, then the resultant polymer is referred to herein as blocked or capped. The unblocked polymer, conversely, has a terminal carboxylic group.

In one aspect, linear lactide/glycolide polymers are used; however branched polymers can be used as well. In certain aspects, high-molecular-weight polymers (e.g., i.v.>1 dL/g as measured in chloroform at a concentration of 0.5 g/dL at 30° C.) can be used for medical devices, for example, to meet strength requirements. In other aspects, low-molecular weight polymers (e.g., i.v.<1 dL/g as measured in chloroform at a concentration of 0.5 g/dL at 30° C.) can be used for drug-delivery and vaccine delivery products where resorption time and not material strength is more important. The lactide portion of the polymer has an asymmetric carbon. Commercially racemic DL-, L-, and D-polymers are available. The L-polymers are more crystalline and resorb slower than DL-polymers. In addition to copolymers comprising glycolide and DL-lactide or L-lactide, copolymers of L-lactide and DL-lactide are available. Additionally, homopolymers of lactide or glycolide are available. Also, the lactide monomer can also contain alkyl groups.

In the case when the biodegradable polymer is poly(lactide-co-glycolide), poly(lactide), or poly(glycolide), the amount of lactide and glycolide in the polymer can vary. In one aspect, the biodegradable polymer contains 0 to 100 mole %, 40 to 100 mole %, 50 to 100 mole %, 60 to 100 mole %, 70 to 100 mole %, or 80 to 100 mole % lactide and from 0 to 100 mole %, 0 to 60 mole %, 10 to 40 mole %, 20 to 40 mole %, or 30 to 40 mole % glycolide, wherein the amount of lactide and glycolide is 100 mole %. In one aspect, the biodegradable polymer can be poly(lactide), 85:15 poly(lactide-co-glycolide), 75:25 poly(lactide-co-glycolide), or 65:35 poly(lactide-co-glycolide) where the ratios are mole ratios.

In one aspect, when the biodegradable polymer is poly(lactide-co-glycolide), poly(lactide), or poly(glycolide), the polymer has an intrinsic viscosity of from 0.15 to 1.5 dL/g, 0.25 to 1.5 dL/g, 0.25 to 1.0 dL/g, 0.25 to 0.8 dL/g, 0.25 to 0.6 dL/g, or 025 to 0.4 dL/g as measured in chloroform at a concentration of 0.5 g/dL at 30° C.

Pharmaceutical Compositions

In a further embodiment of the present invention, the modified peptides and polymer-based delivery systems according to the subject invention are admixed with an appropriate pharmaceutical carrier suitable for administration in primates, especially humans, to provide pharmaceutical compositions.

Pharmaceutically acceptable carriers which can be employed in the present pharmaceutical compositions can be any and all solvents, dispersion media, isotonic agents and the like. Except insofar as any conventional media, agent, diluent or carrier is detrimental to the recipient or to the therapeutic effectiveness of the polymer-based delivery system or therapeutic peptide or other bioactive agent encapsulated therein, its use in the pharmaceutical compositions of the present invention is appropriate.

The carrier can be liquid, semi-solid, e.g., pastes, or solid carriers. Examples of carriers include oils, water, saline solutions, alcohol, sugar, gel, lipids, liposomes, resins, porous matrices, binders, fillers, coatings, preservatives and the like, or combinations thereof.

In a further embodiment of the present invention, the modified peptides and polymer-based delivery systems according to the subject invention can be administered as a powder without carrier.

Methods of Treatment

In a further aspect of the present invention, methods are provided for treating a disease in a vertebrate, preferably a mammal, preferably a primate, with human subjects being an especially preferred embodiment, by administering a peptide formulation of the invention desirable for treating such disease.

EXPERIMENTAL

Example 1

Formulation of Model Peptides

Manufacturing Process:
The peptide-loaded microparticles were prepared using a standard solvent extraction method. Approximately 200 mg of peptide was dissolved in 2 grams of DMSO. Separately, 2 g of poly(lactide-co-glycolide (PLG) was dissolved in 10 g of dichloromethane. The peptide solution was then added to the polymer solution while homogenizing at high revolutions per minute (rpm) using an IKA homogenizer. The peptide/polymer phase was next dispersed into a continuous phase consisting of 3 g of poly(vinyl alcohol) (PVA) and 2.7 g of dichloromethane in 150 mL distilled water by homogenizing at 700 rpm using a Silverson L4RT mixing assembly. Once the droplets had been sufficiently formed (3 minutes) the emulsion was diluted with 1 L of distilled water and stirred on a stirplate for 1 hour, allowing the extraction of the dichloromethane and solidification of the PLG microparticles. Thereafter, the microparticles were isolated by passing the suspension through a 125 micron sieve and collecting microparticles on a 20-micron sieve. The collected microparticles were then lyophilized to remove residual water. The finished product was a white to off-white free-flowing powder and was subsequently stored at −20° C.

Drug Content:

The drug content was determined by carefully extracting peptide from the PLG microparticle formulations. Typically, PLG formulations are dissolved in an appropriate organic solvent (or the polymer is hydrolyzed) and the drug is extracted into a suitable aqueous buffer. Drug in the extract is then quantified by HPLC. The concentration value is used to determine the amount of drug contained in the microparticle, which is reported as weight percent (wt %).

In Vitro Release:

In-vitro release analysis consisted of placing samples of the microparticle formulations into an appropriate receiving fluid (PBS at pH 7.4) maintained at 37° C. with mild agitation. The pH of the receiving fluid was checked routinely to assure that the PBS maintains a pH of 7.4. The receiving fluid was exchanged at various time points and the amount of peptide released into the receiving fluid was quantified by HPLC. Control studies were performed to ensure the stability of the peptide in the receiving fluid once released.

Microparticle Size

The mean size and size distribution of the microparticle formulations was determined using a Beckman Coulter LS 13 320 Laser Diffraction Particle Size Analyzer.

Figure 1:
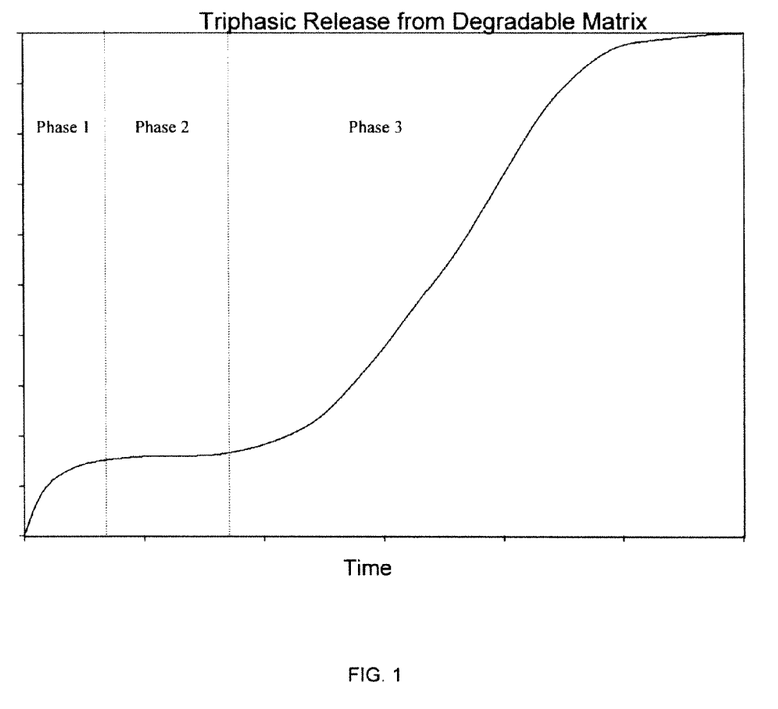
Figure 2:
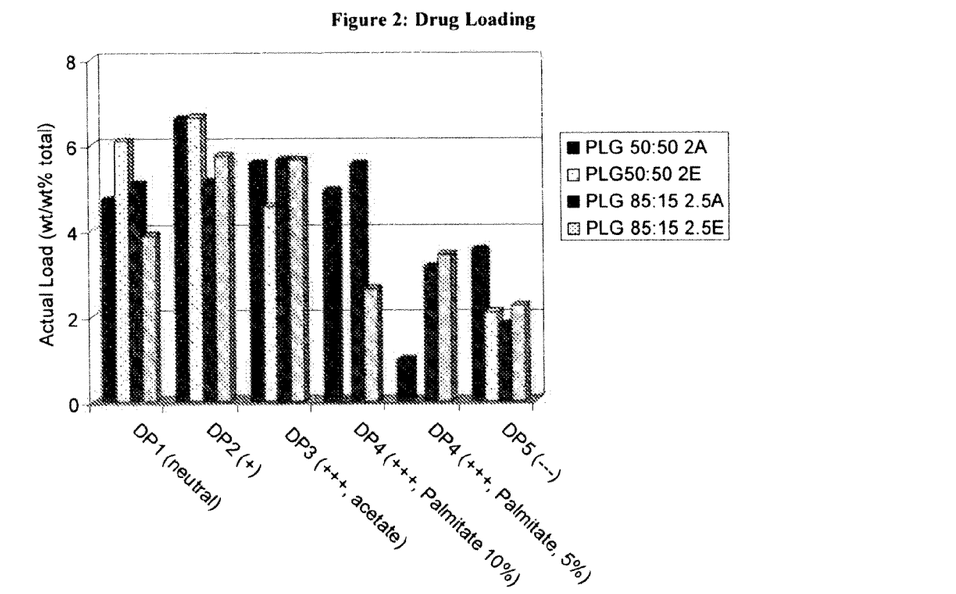
Figure 3:
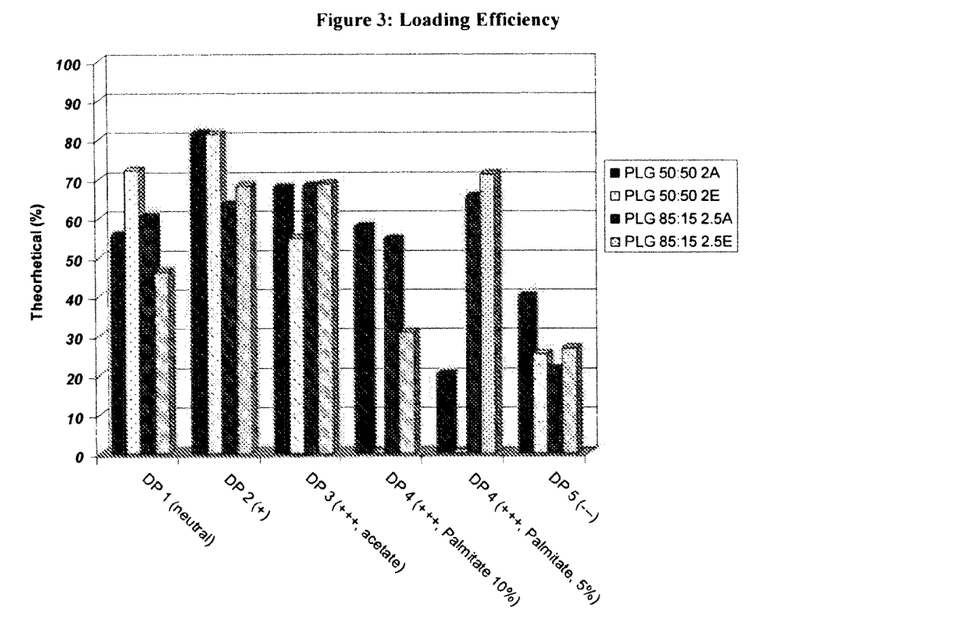

FIGS. 2 and 3 show the effect of charge on drug load and loading efficiency. Within the variation of the data, the drug load and loading efficiency were consistent and similar across the neutral and positively charged peptides. The negatively charged peptide (DP5) was incorporated (loaded) less efficiently when compared to the other peptides studied.

Figure 4:
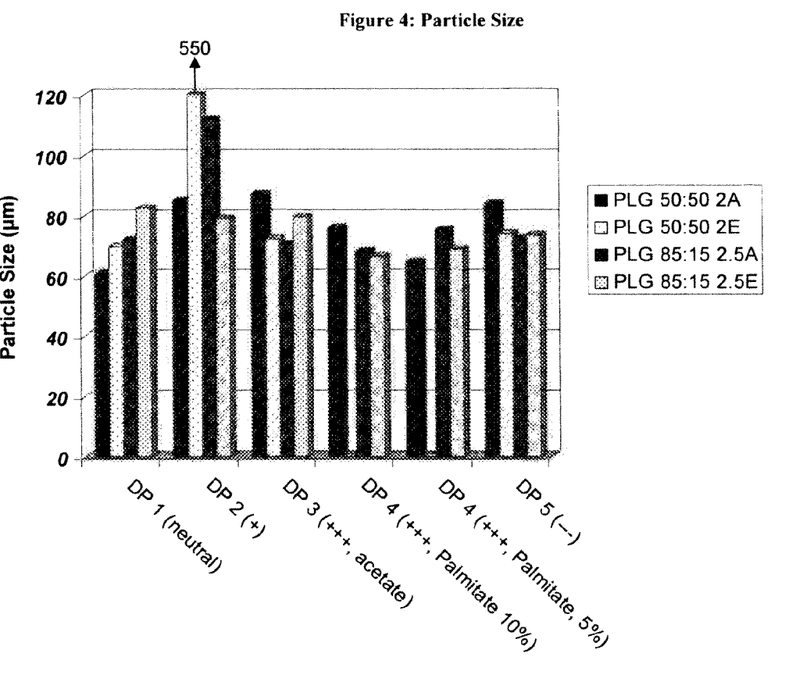

FIG. 4 shows that, with the exception of DP2 in the microparticle formulation containing an ester-terminated 50:50 poly(lactide-co-glycolide) with an approximate i.v. of 0.2 dL/g as measured in chloroform at a concentration of 0.5 g/dL at 30° C., particle size was unaffected by the peptide incorporated.

Figure 5:
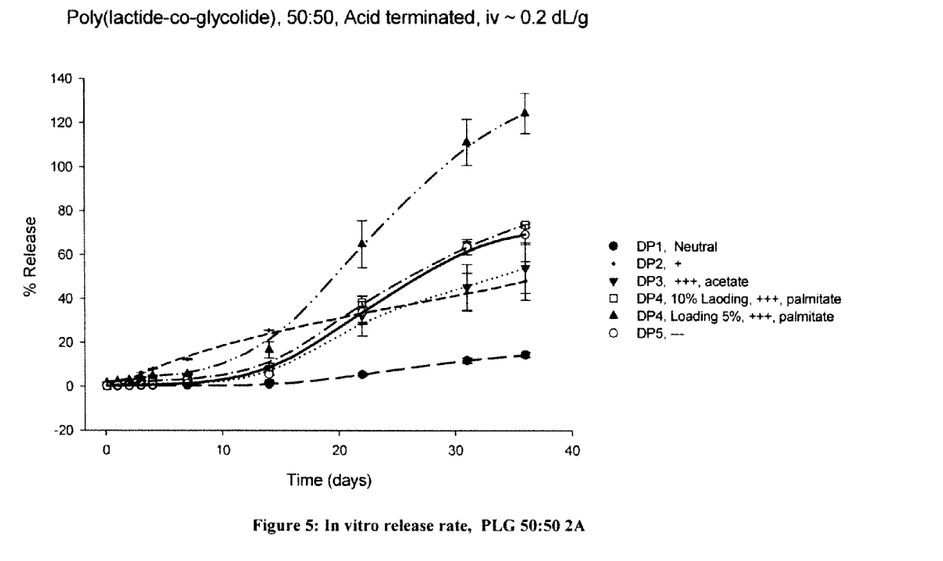
Figure 6:
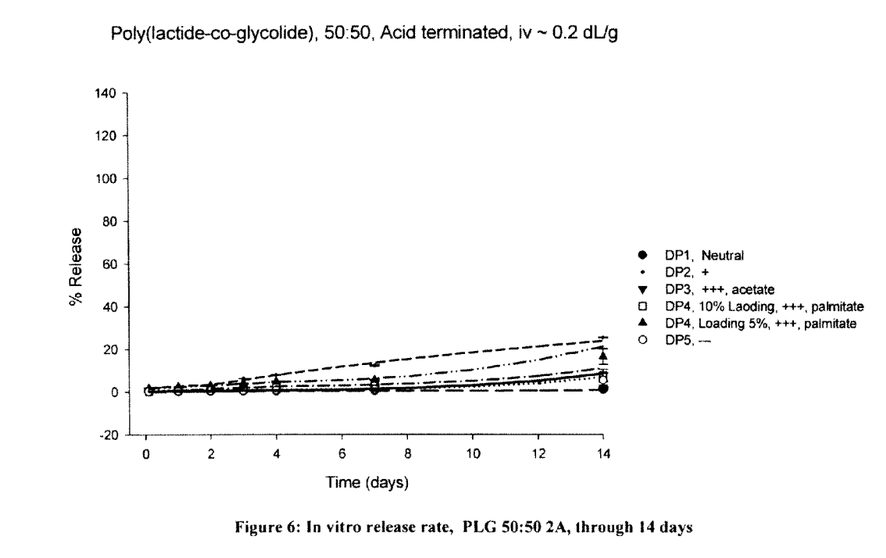

FIGS. 5 and 6 demonstrate the effect of peptide charge on release from a microparticle formulation containing an acid-terminated 50:50 poly(lactide-co-glycolide) with an approximate i.v. of 0.2 dL/g as measured in chloroform at a concentration of 0.5 g/dL at 30° C. The charged peptides release at a consistently faster rate when compared to the neutral peptide. It may also be noted that the higher charge-density peptides (DP3 DP4, DP5 verses DP2) released more rapidly. It is also of note that no "burst" was observed form this polymer-based delivery system.

Figure 7:
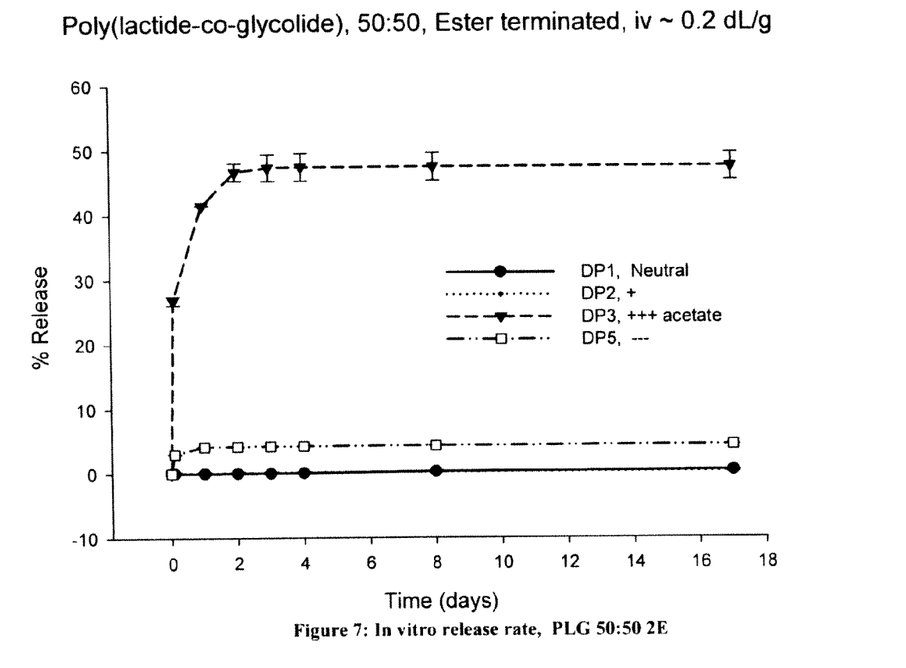
FIG. 7 shows the release rate as percent release (y-axis) of four peptides (DP1, DP2, DP3, and DP5) with a neutral, positive (+) or negative (−) charge overall over 17 days (x-axis) from a microparticle, polymer-based formulation containing an ester-terminated, 50:50 poly(lactide-co-glycolide) with an approximate i.v. of 0.2 dig as measured in chloroform at a concentration of 0.5 g/dL at 30° C. Unless otherwise noted, each peptide molecule was loaded into the polymer as an acetate salt.

FIG. 7 shows the release profiles form a similar microparticle, polymer-based formulation, an ester-terminated 50:50 poly(lactide-co-glycolide) with an approximate i.v. of 0.2 dL/g as measured in chloroform at a concentration of 0.5 g/dL at 30° C. While the neutral and negatively charged peptide showed very little release over the period studied, the positively charged peptide exhibited a significant burst from the formulation. Further, the greater the positive charge (higher charge density) the more significant the effect on the release rate.

Figure 8:
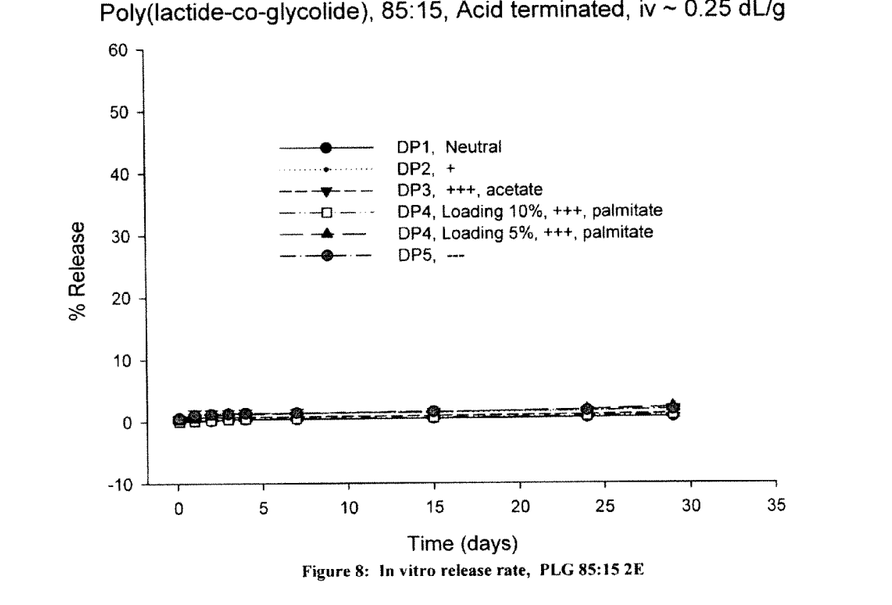
FIG. 8 shows the release rate as percent release (y-axis) of five peptides (DP1, DP2, DP3, DP4, and DP5) with a neutral, positive (+) or negative (−) charge overall over 29 days (x-axis) from a microparticle, polymer-based formulation containing an acid terminated 85:15 poly(lactide-co-glycolide) with an approximate i.v. of 0.25 dL/g as measured in chloroform at a concentration of 0.5 g/dL at 30° C. Unless otherwise noted, each peptide molecule was loaded into the polymer as an acetate salt.

FIG. 8 shows the release of the peptides from a microparticle formulation containing an acid-terminated 85:15 poly (lactide-co-glycolide) with an approximate i.v. of 0.25 dL/g as measured in chloroform at a concentration of 0.5 g/dL at 30° C. Over the period studied, release of peptide was not observed from any microparticle formulation.

Figure 9:
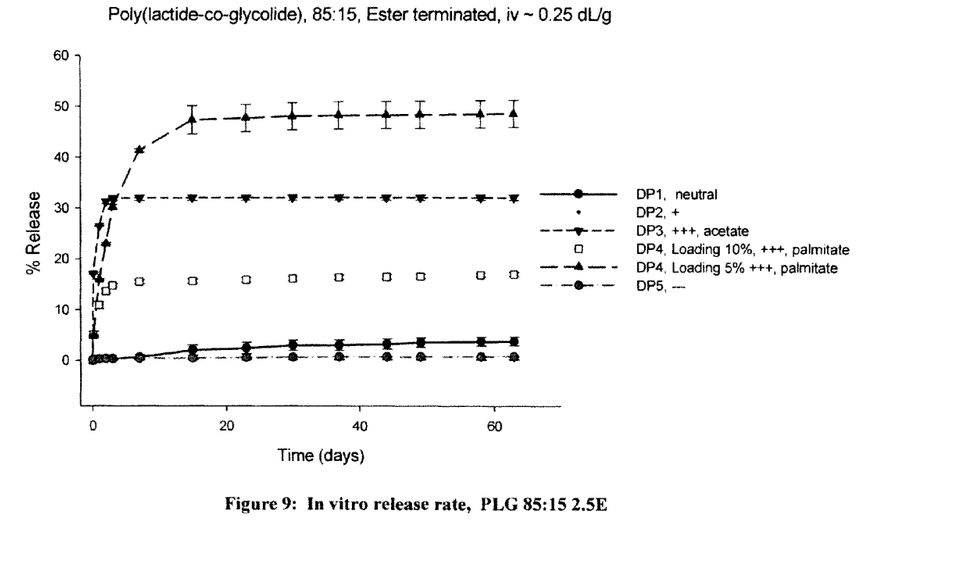
FIG. 9 shows the release rate as percent release (y-axis) of five peptides (DP1, DP2, DP3, DP4, and DP5) with a neutral, positive (+) or negative (−) charge overall over 65 days (x-axis) from a microparticle, polymer-based formulation containing an ester-terminated 85:15 poly(lactide-co-glycolide) with an approximate i.v. of 0.25 dL/g as measured in chloroform at a concentration of 0.5 g/dL at 30° C. Unless otherwise noted, each peptide molecule was loaded into the polymer as an acetate salt.
Figure 10:
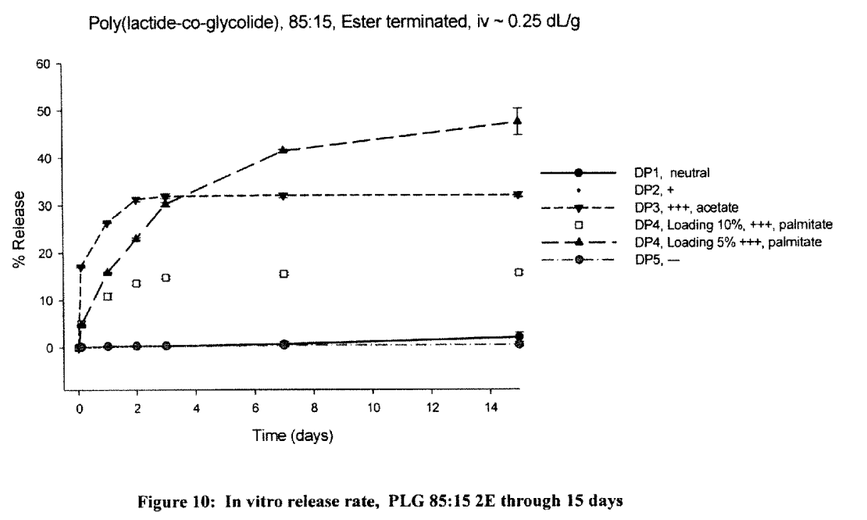
FIG. 10 shows the release rate as percent release (y-axis) of five peptides (DP1, DP2, DP3, DP4, and DP5) with a neutral, positive (+) or negative (−) charge overall over 15 days (x-axis) from a microparticle, polymer-based formulation containing an ester-terminated 85:15 poly(lactide-co-glycolide) with an approximate i.v. of 0.25 dL/g as measured in chloroform at a concentration of 0.5 g/dL at 30° C. Unless otherwise noted, each peptide molecule was loaded into the polymer as an acetate salt.

FIG. 9 shows the release of the peptides from a microparticle formulation containing an ester-terminated 85:15 poly (lactide-co-glycolide) with an approximate i.v. of 0.25 dL/g as measured in chloroform at a concentration of 0.5 g/dL at 30° C. While the neutral and negatively charged peptide showed very little release over the period studied, the positively charged peptide exhibited a more significant release from the microparticle formulation. The greater the positive charge (higher charge density) the more significant the effect on the release rate.

Example 2

Exemplary Modifications of Parent Peptides

Calcitonin

Calcitonin is a hormone used in the treatment of osteoporosis. The amino acid sequence of human Calcitonin is Cys-Gly-Asn-Leu-Ser-Thr-Cys-Met-Leu-Gly-Thr-Tyr-Thr-Gln-Asp-Phe-Asn-Lys-Phe-His-Thr-Phe-Pro-Gln-Thr-Ala-Ile-Gly-Val-Gly-Ala-Pro (set forth as SEQ ID NO:1).

The pI of Calcitonin is modified to enhance its use in a controlled released formulation by adding a tri-lysine moiety at the N-terminus to increase its encapsulation efficacy (set forth as SEQ ID NO:2). Alternatively, to increase its initial burst from an ester-terminated polyester, the glycine residues are replaced with lysines (set forth as SEQ ID NO:3). To increase erosional release from an acid-terminated polyester, the glycine residues are replaced with aspartic acids (set forth as SEQ ID NO:4).

Leuprolide

Leuprolide is a gonadotropin-releasing hormone agonist that may be used in the treatment of prostate cancer or endometriosis. The amino acid sequence of Leuprolide is Glu-His-Trp-Ser-Tyr-DLeu-Leu-Arg-Pro-NHEt (set forth as SEQ ID NO:5).

The pI of Leuprolide is modified to enhance its use in a controlled released formulation by replacing the glutamic acid with glutamine (set forth as SEQ ID NO:6) to increase its diffusional release from an ester-terminated polyester and/or replacing the arginine with aspartic acid (set forth as SEQ ID NO:7) to decrease diffusional release from an ester-terminated polyester.

Octreotide

Octreotide is an octapeptide that may be used as an inhibitor of growth hormone and/or the treatment of acromegaly. The amino acid sequence of Octreotide is DPhe-Cys-Phe-DTrp-Lys-Thr-Cys-Thr (set forth as SEQ ID NO:8).

The threonine is replaced with lysine (set forth as SEQ ID NO:9) to modify the pI of Octreotide and to enhance its use in a controlled-released formulation, e.g., to increase the encapsulation efficiency and drug load of Octreotide.

All citations are expressly incorporated herein in their entirety by reference.

We claim:

1. A controlled-release pharmaceutical formulation comprising a modified bioactive agent encapsulated by a polymer selected from poly(lactide-co-glycolide), poly(lactide), poly(glycolide), polycaprolactone, poly(lactide-co-caprolactone), poly(lactide-co-glycolide-co-caprolactone), poly(glycolide-co-caprolactone), or a mixture thereof, wherein said modified bioactive agent is a peptide having the amino acid sequence selected from the group consisting of: SEQ ID NO:2, SEQ ID NO:3, SEQ ID NO:4, SEQ ID NO:6, SEQ ID NO:7 and SEQ ID NO:9.

2. The controlled-release pharmaceutical formulation according to claim 1, wherein said polymer is poly(lactide-co-glycolide).

3. The controlled-release pharmaceutical formulation according to claim 1 or 2, wherein said modified bioactive agent is a peptide having the amino acid sequence set forth in SEQ ID NO:2.

4. The controlled-release pharmaceutical formulation according to claim 1 or 2, wherein said modified bioactive agent is a peptide having the amino acid sequence set forth in SEQ ID NO:3.

5. The controlled-release pharmaceutical formulation according to claim 1 or 2, wherein said modified bioactive agent is a peptide having the amino acid sequence set forth in SEQ ID NO:4.

6. The controlled-release pharmaceutical formulation according to claim 1 or 2, wherein said modified bioactive agent is a peptide having the amino acid sequence set forth in SEQ ID NO:6.

7. The controlled-release pharmaceutical formulation according to claim 1 or 2, wherein said modified bioactive agent is a peptide having the amino acid sequence set forth in SEQ ID NO:7.

8. The controlled-release pharmaceutical formulation according to claim 1 or 2, wherein said modified bioactive agent is a peptide having the amino acid sequence set forth in SEQ ID NO:9.

* * * * *

SEQUENCE LISTING

<160> NUMBER OF SEQ ID NOS: 9

<210> SEQ ID NO 1
<211> LENGTH: 32
<212> TYPE: PRT
<213> ORGANISM: Homo sapiens

<400> SEQUENCE: 1

Cys Gly Asn Leu Ser Thr Cys Met Leu Gly Thr Tyr Thr Gln Asp Phe
1               5                   10                  15

Asn Lys Phe His Thr Phe Pro Gln Thr Ala Ile Gly Val Gly Ala Pro
            20                  25                  30

<210> SEQ ID NO 2
<211> LENGTH: 35
<212> TYPE: PRT
<213> ORGANISM: Homo sapiens

<400> SEQUENCE: 2

Lys Lys Lys Cys Gly Asn Leu Ser Thr Cys Met Leu Gly Thr Tyr Thr
1               5                   10                  15

Gln Asp Phe Asn Lys Phe His Thr Phe Pro Gln Thr Ala Ile Gly Val
            20                  25                  30

Gly Ala Pro
        35

<210> SEQ ID NO 3
<211> LENGTH: 32
<212> TYPE: PRT
<213> ORGANISM: Homo sapiens

<400> SEQUENCE: 3

Cys Lys Asn Leu Ser Thr Cys Met Leu Lys Thr Tyr Thr Gln Asp Phe
1               5                   10                  15

Asn Lys Phe His Thr Phe Pro Gln Thr Ala Ile Lys Val Lys Ala Pro
            20                  25                  30

<210> SEQ ID NO 4
<211> LENGTH: 32
<212> TYPE: PRT
<213> ORGANISM: Homo sapiens

<400> SEQUENCE: 4

Cys Asp Asn Leu Ser Thr Cys Met Leu Asp Thr Tyr Thr Gln Asp Phe
1               5                   10                  15

Asn Lys Phe His Thr Phe Pro Gln Thr Ala Ile Asp Val Asp Ala Pro
            20                  25                  30

<210> SEQ ID NO 5
<211> LENGTH: 9
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: D amino acid
<220> FEATURE:
<221> NAME/KEY: MISC_FEATURE
<222> LOCATION: (9)..(9)
<223> OTHER INFORMATION: NHEt

<400> SEQUENCE: 5

Glu His Trp Ser Tyr Leu Leu Arg Pro
1               5

```
<210> SEQ ID NO 6
<211> LENGTH: 9
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: D amino acid
<220> FEATURE:
<221> NAME/KEY: MISC_FEATURE
<222> LOCATION: (9)..(9)
<223> OTHER INFORMATION: NHEt

<400> SEQUENCE: 6

Gln His Trp Ser Tyr Leu Leu Arg Pro
1               5

<210> SEQ ID NO 7
<211> LENGTH: 9
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: D amino acid
<220> FEATURE:
<221> NAME/KEY: MISC_FEATURE
<222> LOCATION: (9)..(9)
<223> OTHER INFORMATION: NHEt

<400> SEQUENCE: 7

Glu His Trp Ser Tyr Leu Leu Asp Pro
1               5

<210> SEQ ID NO 8
<211> LENGTH: 8
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: D amino acid
<220> FEATURE:
<221> NAME/KEY: MISC_FEATURE
<222> LOCATION: (4)..(4)
<223> OTHER INFORMATION: D amino acid

<400> SEQUENCE: 8

Phe Cys Phe Trp Lys Thr Cys Thr
1               5

<210> SEQ ID NO 9
<211> LENGTH: 8
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: D amino acid
<220> FEATURE:
<221> NAME/KEY: MISC_FEATURE
<222> LOCATION: (4)..(4)
<223> OTHER INFORMATION: D amino acid

<400> SEQUENCE: 9

Phe Cys Phe Trp Lys Lys Cys Lys
1               5
```